(12) United States Patent
Liu et al.

(10) Patent No.: US 10,016,131 B2
(45) Date of Patent: Jul. 10, 2018

(54) EYE TRACKING SYSTEM AND METHOD TO DETECT THE DOMINANT EYE

(71) Applicant: SENSOMOTORIC INSTRUMENTS GESELLSCHAFT FUR INNOVATIVE SENSORIK MBH, Teltow (DE)

(72) Inventors: Kun Liu, Berlin (DE); Walter Nistico, Berlin (DE); Hao Qin, Berlin (DE)

(73) Assignee: SENSOMOTORIC INSTRUMENTS GESELLSCHAFT FUR INNOVATIVE SENSORIK MBH, Teltow (DE)

( * ) Notice: Subject to any disclaimer, the term of this patent is extended or adjusted under 35 U.S.C. 154(b) by 0 days.

(21) Appl. No.: 15/526,005

(22) PCT Filed: Oct. 7, 2015

(86) PCT No.: PCT/EP2015/073185
§ 371 (c)(1),
(2) Date: May 11, 2017

(87) PCT Pub. No.: WO2016/074861
PCT Pub. Date: May 19, 2016

(65) Prior Publication Data
US 2017/0340205 A1 Nov. 30, 2017

(30) Foreign Application Priority Data
Nov. 14, 2014 (EP) ..................................... 14193277

(51) Int. Cl.
*G06K 9/00* (2006.01)
*A61B 3/113* (2006.01)
(Continued)

(52) U.S. Cl.
CPC ................ *A61B 3/113* (2013.01); *A61B 3/08* (2013.01); *A61B 3/14* (2013.01); *G06T 7/0012* (2013.01);
(Continued)

(58) Field of Classification Search
None
See application file for complete search history.

(56) References Cited

U.S. PATENT DOCUMENTS 8,807,749 B2 * 8/2014 Fateh ....................... A61B 3/00
351/205
2010/0110374 A1 5/2010 Raguin et al.
(Continued)

FOREIGN PATENT DOCUMENTS

WO 2012/021967 A1 2/2012

OTHER PUBLICATIONS

International Search Report for PCT/EP2015/073185 dated Jan. 14, 2016 [PCT/ISA/210].
(Continued)

*Primary Examiner* — Mark Roz
(74) *Attorney, Agent, or Firm* — Ronald Fernando

(57) ABSTRACT

The invention relates to an eye tracking system (10) and a method for operating an eye tracking system (10) for determining if one of a left and a right eye of a user is dominant, wherein at least one image of the left and the right eye of the user is captured (S30), based on the at least one image and according to a predefined accuracy function a left accuracy score for the left eye (S34a) and a right accuracy score for the right eye (S34c) is determined and it is determined if one of the left and the right eye of the user is dominant in dependency of at least the left and the right accuracy score (S36). Thereby user-specific properties relating to his eyes can be provided and considered when performing eye track-
(Continued)

Figure 1:
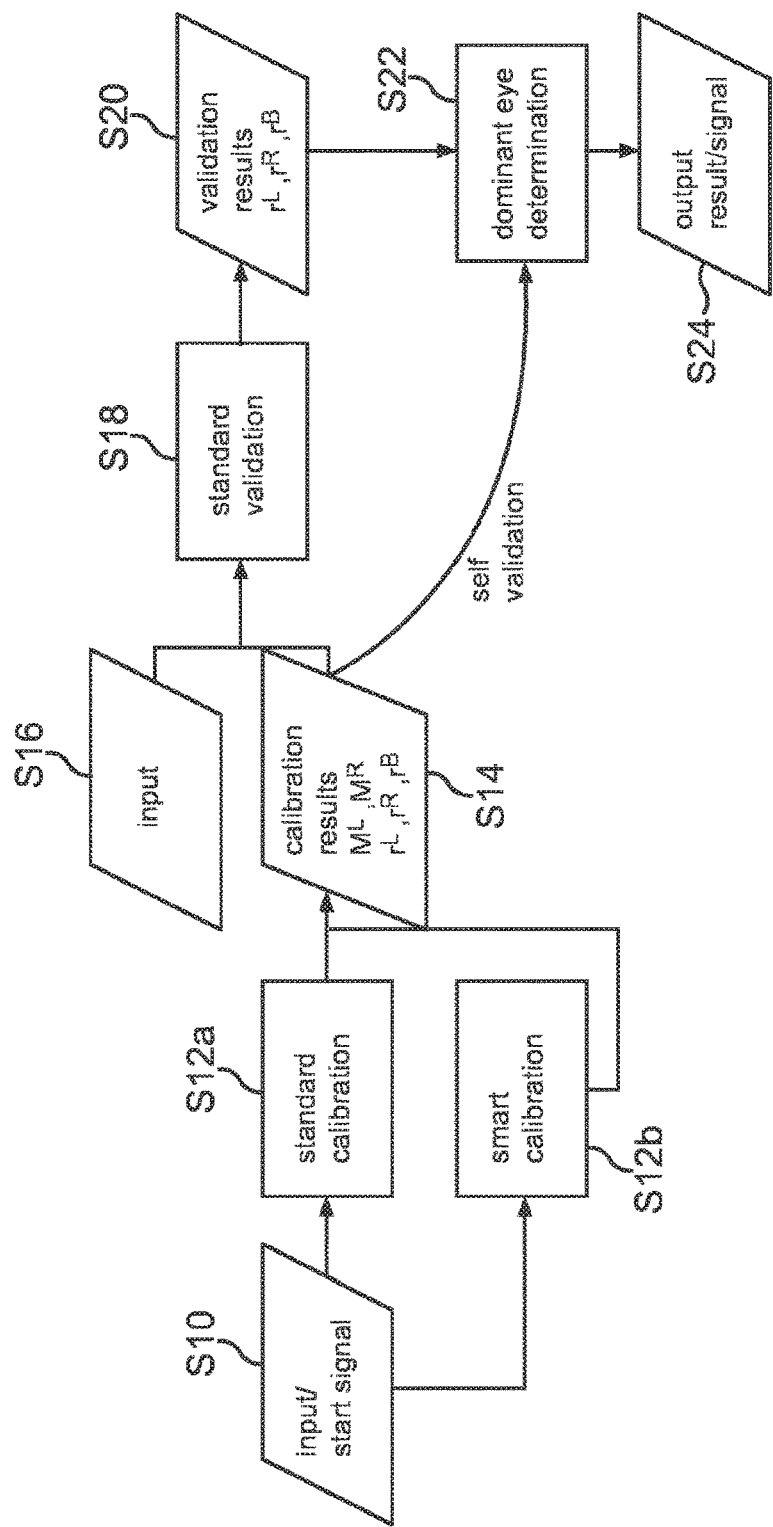

ing so that the robustness and accuracy of eye tracking can be enhanced.

16 Claims, 4 Drawing Sheets

(51) Int. Cl.
*A61B 3/14* (2006.01)
*A61B 3/08* (2006.01)
*G06T 7/00* (2017.01)
*G06T 7/70* (2017.01)

(52) U.S. Cl.
CPC ...... *G06T 7/70* (2017.01); *G06T 2207/30041* (2013.01)

(56) References Cited

U.S. PATENT DOCUMENTS

| | | | |
|---|---|---|---|
| 2013/0107207 A1 | 5/2013 | Zhao et al. | |
| 2014/0016090 A1* | 1/2014 | Bonnin | A61B 3/113 351/204 |
| 2014/0085608 A1 | 3/2014 | Clopton | |
| 2016/0287069 A1* | 10/2016 | Haddadi | A61B 3/113 |

OTHER PUBLICATIONS

Written Opinion for PCT/EP2015/073185 dated Jan. 14, 2016 [PCT/ISA/237].

\* cited by examiner

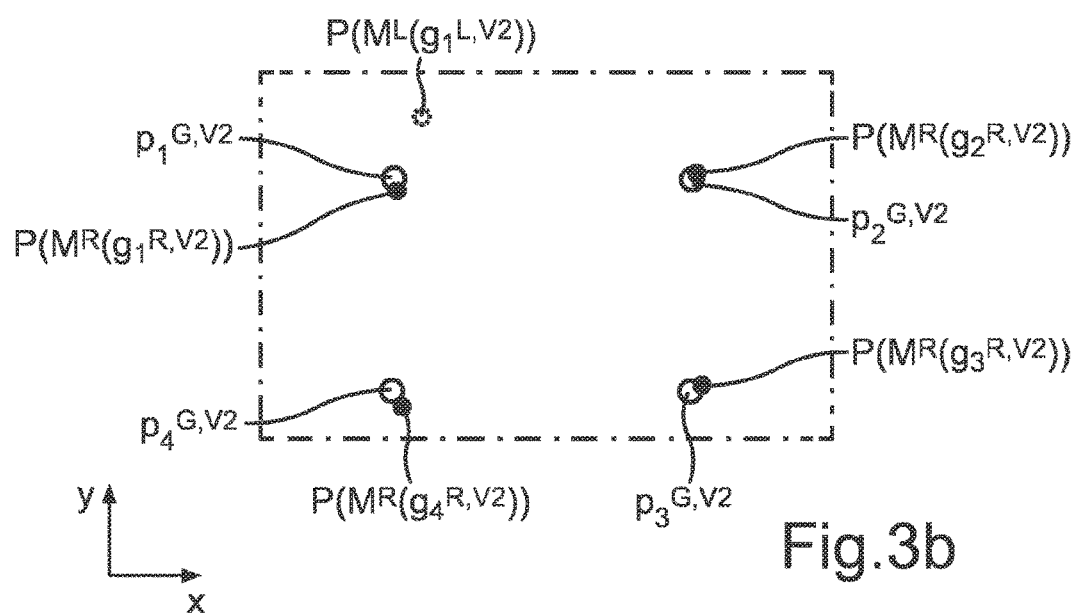

EYE TRACKING SYSTEM AND METHOD TO DETECT THE DOMINANT EYE

CROSS REFERENCE TO RELATED APPLICATIONS

This application is the national stage entry of International Application No. PCT/EP2015/073185, filed on Oct. 7, 2015, which claims priority from European Patent Application No. 14193277.2, filed on Nov. 14, 2014, the contents of both of which are incorporated by reference herein.

The present invention relates to an eye tracking system and a method for operating an eye tracking system.

Known eye tracking systems and eye tracking devices usually capture images of the eyes of a user and therefrom determine a gaze direction, a point of regard or other eye features. For this purpose, the position, orientation or other properties of the eyes of a user can be determined. To be able to take into account user-specific properties, e.g. the shift between the optical axis and the visual axis of the eye, a calibration procedure can be performed for calibrating the eye tracking system. During such a calibration procedure, usually calibration points, also called stimulus points, are shown on a display in a timely manner and the user has to fixate these calibration points with his eyes. Meanwhile, the eye tracking system captures images of the eyes of the user, calculates the gaze or point of regard, compares the calculated points of regard to the positions of the shown calibration points and determines a map that minimizes the difference between the calculated points of regard and the shown calibration points. So, by taking into account user-specific properties of the eyes the eye tracking quality can be enhanced.

The object of the present invention is to provide a method for operating an eye tracking system and an eye tracking system, which can provide more user-specific properties relating to his eyes, especially which can enhance the robustness or accuracy of eye tracking.

This object is solved by a method for operating an eye tracking device for determining if one of a left and a right eye of a user is dominant and an eye tracking system according to the independent claims. Advantageous embodiments of the invention are presented in the dependent claims.

According to the method for operating an eye tracking system for determining if one of a left and a right eye of a user is dominant in accordance with the invention, at least one image of the left and the right eye of the user is captured and based on the at least one image and according to a predefined accuracy function a left accuracy score for the left eye and a right accuracy score for the right eye are determined. Furthermore, it is determined if one of the left and the right eye of the user is dominant in dependency on at least the left and the right accuracy score.

By determining the left and the right accuracy score, especially where these accuracy scores give information about the tracking accuracy with respect to the left and the right eye respectively and separately, it can easily be determined whether there is a dominant eye or not. Knowing the dominant eye can enormously enhance the tracking quality. The reason for this is that usually data relating to both eyes are used for eye tracking and therefore are weighted equally. If there is a dominant or on the other hand a weak eye, this can result in distorting the eye tracking results tremendously, for example with respect to the calculated point of regard. Advantageously, according to the invention it is possible to determine if there is a dominant eye and to use this result, for example, for eye tracking purposes but also for diagnostic purposes. Detecting the dominant eye of a person can be used to diagnose eye vergence pathologies such as Strabismus and Amblyopia. Furthermore, the point-of-regard-accuracy of the eye tracking system can be improved by automatically detecting if a strong eye dominance or presence of eye vergence pathologies results in an eye being unable to accurately fixate objects. Hence, for example the eye tracking data associated with a non-dominant eye can be discarded or weighted less than the eye tracking data associated with the dominant eye.

The respective accuracy scores are determined on the basis of image data of the at least one image, wherein an image of the left eye and an image of the right eye can be captured and processed separately, e.g. the images of the left and the right eye can be captured by two separate cameras or image sensors, or on the other hand it is also possible to capture one common image of the left and the right eye, which is processed for deriving image data relating to the left eye for determining the left accuracy score and for deriving image data relating to the right eye for determining the right accuracy score. It's also preferred to capture more than one single image, especially plenty of images, e.g. hundreds of images, on the basis of which the left and right accuracy score is determined, because then the accuracy and reliability of the outcome of the determination of the dominant eye is significantly higher.

The accuracy function according to which the respective accuracy scores are calculated can be a predefined mathematical formula, an algorithm, a look-up-table, and so on, which has image data of the respective eye or data of the respective eye calculated on the basis of the image as input and gives the respective accuracy score as output. Furthermore, the method according to the invention can be performed, especially automatically, during a calibration procedure and/or validation procedure for validating calibration results. Also at least part of the method can be performed after such procedures using results of the calibration and/or validation procedure. For example, errors, like a residual error for the left eye, the right eye and a binocular residual error, calculated during a calibration procedure and/or validation procedure can serve as the respective accuracy score and the functions and/or algorithms for calculating these errors could then constitute the accuracy function.

In an advantageous embodiment of the invention, a signal is provided and/or outputted in dependency on the left and right accuracy score, especially a signal indicating the identity of the dominant eye. This signal can, for example, be used to output the information about the dominant eye to the user or another person, e.g. on a screen, for diagnosis purposes. Also, the signal can be used to indicate whether captured data relating to both eyes or only captured data relating to the left or the right eye should be used for eye tracking. So advantageously, the result of the determination whether there is a dominant eye can enhance the functionalities of diagnostic devices and the capabilities and accuracies of eye tracking devices.

Furthermore, based on the at least one image and according to the predefined accuracy function, a binocular accuracy score for the left and the right eye can be determined, and it is determined if one of the left and the right eye of the user is dominant in dependency on the left, right and binocular accuracy score. By taking into account the binocular accuracy score, which defines e.g. an accuracy score for the binocular gaze or binocular point of regard, that is related to the left and the right eye, a decision whether there is a dominant eye can be made more reliably. Moreover, the above-mentioned signal can be provided and outputted in dependency on the left, right and binocular accuracy score. Based on the signal, a channel, namely a left channel, a right channel or a binocular channel, can then be chosen for eye tracking, especially wherein the left channel provides eye data relating to the left eye, e.g. the gaze direction of the left eye or the point of regard of the left eye, the right channel similarly provides data with respect to the right eye and the binocular channel provides data with respect to both eyes, e.g. the binocular gaze or binocular point of regard. Beneficially, based on the best accuracy score the best of these three channels can be chosen for eye tracking. Thereby, the eye tracking accuracy and robustness can be optimized.

In general the left gaze direction can be calculated on the basis of image data of the at least one image relating to the left eye. The left point of regard is determined as the intersection of the determined gaze vector of the left eye with a predefined plane. This plane can be e.g. the display or a screen of a monitor, especially a remote monitor, or the display or a screen of a head mounted display device. In case of 3D capable display devices or in case there is a lens or other optical system in between the display device and the user's eyes the plane can also be a virtual image plane. The coordinates of this plane is known to the eye tracking system and therefore the intersection of the gaze vector and the plane can be calculated as the point of regard. The same applies for the right gaze direction and the right point of regard. The binocular gaze direction is the averaged gaze direction of the left and the right eye. The binocular point of regard can be calculated in several ways for example the binocular point of regard can be calculated as the intersection of the binocular gaze vector with the predefined plane or as the middle of the right and left point of regard on the predefined plane or as an projection of the intersection point of the left and the right gaze vectors onto the predefined plane, e.g. in the direction of the binocular gaze direction.

Moreover, the left accuracy score is a measure for a deviation of a point of regard of the left eye from a left set point of regard, and the right accuracy score is a measure for a deviation of a point of regard of the right eye from a right set point of regard and the, especially optional, binocular accuracy score is a measure for a deviation of a binocular point of regard of the left and the right eye from a binocular set point of regard. Or in other words, these deviations can be calculated and the left, right and optionally also the binocular accuracy score can be determined or calculated in dependency of the respective deviations, especially wherein other influencing parameters can be considered when determining the respective accuracy scores as well. To determine these deviations, a procedure similar to a calibration procedure can be used. Thereby, calibration points, also called stimulus points, which correspond to the set points of regard, can be shown on a display and a left, right and binocular point of regard and their respective deviations or differences to the set points of regard can be determined. Then, these deviations can be used to calculate the accuracy score for the left and the right eye and the binocular accuracy score for both eyes. Besides these deviations of the points of regard from set points of regard, further influencing variables can be considered when determining the respective accuracy score, like the number of validly tracked points of regard. The calculation of the respective accuracy scores in dependency on these influencing variables or other variables can be defined by the predefined accuracy function. As this procedure for determining the respective accuracy scores is similar to a calibration procedure and/or validation procedure it can be advantageously be embedded in a calibration and/or validation procedure, which makes it particularly time efficient and minimises the computing effort and computing time.

Furthermore, in general the left set point of regard, the right set point of regard and the binocular point of regard, which can be e.g. shown on a display, can be—but need not—be different in their positions. For example, first a number of left set points of regard can be shown one after the other on a display and for each shown left set point of regard the corresponding left point of regard of the user can be determined, especially the position of the left point of regard of the user on the display, and therefrom the deviations of each determined left point of regard from the position of the respective left set point of regard can be calculated. After that, a number of right set points of regard can be shown and the right points of regard of the user and the respective deviations can be determined analogously. After that, a number of binocular set points of regard can be shown one after the other and the binocular points of regard of the user for each binocular set point of regard and the respective deviations can be determined analogously as well. But to shorten this procedure, it is very advantageous if instead of separate or different set points for the left eye, right eye and both eyes, shared set points are used for the left, right and both eyes. So, for example one set point can be shown, which then constitutes the left set point of regard, the right set point of regard and optionally the binocular set point of regard at the same time, meaning the right point of regard of the user, the left point of regard of the user and optionally the binocular point of regard of the user is determined while the user is looking at that single set point, and the deviation of the left point of regard from the shown set point is determined, the deviation of the right point of regard from the shown set point is determined and optionally the deviation of the binocular point of regard from the set point is determined. This is then repeated for a number of set points shown one after the other. Consequently, much time can be saved when using shared set points of regard for determining the left, right and optionally binocular point of regard and the respective deviations, wherein this time saving effect is the more beneficial the more set points are shown and by this more comfort can be achieved for the user additionally.

Therefore, it s a preferred and advantageous embodiment of the invention that the left, right and binocular set points of regard are identical and preferably are provided by showing a finite sequence of points, i.e. stimulus points, on a display device of the eye tracking system that the user is required to fixate and/or by showing a smooth and/or continuous motion of a point or other stimulus image on the display device that the user is required to follow with both eyes. For example, a single set point of regard can be shown on a display or a screen as the left, right and binocular set point of regard and then the left point of regard, the right point of regard and the binocular point of regard can be determined by the at least one image captured during the user is fixating the shown set point of regard and the respective accuracy score can be determined from the respective deviations of the determined points of regard from the set point of regard. This can be done for plenty of set points of regard shown in a temporal sequence or even in a smooth motion so that the respective accuracy scores can be determined more precisely.

According to a preferred embodiment of the invention the determination if one of the left and the right eye of the user is dominant is performed during a calibration procedure of the eye tracking system and/or during a validation procedure for validating results of the calibration procedure. As usually a calibration procedure is performed anyway, the results of this procedure can advantageously be used for determining the respective accuracy scores and thereby the dominant eye. Additionally, also the results of a validation procedure can be used for this purpose, which makes the results even more reliable. For example, first a calibration procedure can be performed, during which some calibration points as the set points of regard are shown on a display in a timely manner. While these points are shown, the eye tracking system captures several images of both eyes of the user and defines the parameters of a calibration map that maps the determined points of regard to such calibrated points of regard that minimize the deviation from the shown calibration points. Afterwards, a validation procedure can be performed, during which second set points of regard can be shown on a screen or display the user has to look at and further images are captured while these points are shown. Based on the captured further images and based on the calibration map, the parameters of which were determined in the calibration procedure, again the points of regard of the left, right eye and the binocular point of regard are determined with respect to each second set point and again the error of the left, right and binocular point of regard with respect to each second set point can be calculated. Then, these errors, namely that for the left eye, for the right eye and the binocular error, can be used to determine the respective accuracy scores.

So in general, during the calibration procedure of the eye tracking system several first points of regard of the user are calculated and compared to corresponding first set points of regard, wherein on the basis of this comparison calibration parameters of the eye tracking system are set so that the calculated first points of regard are mapped to corresponding calibrated first points of regard. This is particularly done with respect to the left and the right eye each, i.e. a calibration map is defined for the left eye and the right eye separately, so that information about differences between the left and the right eye properties are not lost.

Furthermore, during the validation procedure, several second points of regard of the user are calculated and compared to corresponding second set points of regard. By means of the validation procedure, the results of the calibration procedure can be validated. In other words, by performing the validation procedure it can be determined whether the calibration was successful or not. So, advantageously, this validation procedure can be used for two purposes, namely for validating the results of the calibration procedure and on the other hand the results or measurements performed during the validation procedure can be used for calculating the respective accuracy scores and thereby determining the dominant eye.

So, preferably, on the basis of the deviation of the calibrated first points of regard from the first set points of regard an error of the calibration procedure for the left eye, the right eye and for both eyes is calculated and/or on the basis of the deviation of the second points of regard from the second set points of regard an error of the validation procedure for the left eye, the right eye and for both eyes is calculated. Advantageously, either only the results of the calibration procedure can be used for determining the dominant eye, which allows for a very quick performance, or the results of the validation procedure can be used, which allows for much higher accuracy and robustness.

In a further embodiment of the invention, during the calibration procedure an optimal subset of calibration points is automatically detected by excluding outliers according to a predefined criterion, preferably by evaluating all the subsets of the calibration points or by finding a randomized consensus. Sometimes it might happen that the user who is required to look at the shown set points might be distracted or otherwise fails to look at the set points so that it is very advantageous to exclude such outliers as they would falsify the result. For example, if five set points are shown, all three-point, four-point and five-point subsets can be listed and analyzed with regard to the respective determined points of regard of the user and then the best subset can be chosen. The same can be done with just a random sample of subsets instead of taking all possible subsets into account, which is advantageous if lots set points are shown.

Additionally, the left, right and binocular accuracy score can be each determined in dependency on whether a left point of regard, right point of regard and binocular point of regard, respectively, can be calculated on the basis of the at least one image and/or the error of the calibration procedure and/or validation procedure for the left eye, the right eye and both eyes, respectively. Sometimes it is not possible to determine the left, right or binocular point of regard, e.g. because one or both eyes cannot be detected in the captured image. Being unable to detect one or both eyes is also a measure for the eye tracking quality. If, for example, for five shown set points of regard the left point of regard can only be determined twice, whereas the right point of regard can be determined five times, the tracking quality for the right eye can be assumed to be much better than the tracking quality for the left eye. So, advantageously, also the information regarding the number of valid calibration points used in model fitting for defining the calibration map or the information regarding the number of well tracked validation points can be considered when calculating the respective accuracy scores. As already mentioned, above all the error of the calibration procedure and/or validation procedure for the left, the right and both eyes is a very good measure for the tracking quality, so it is very advantageous to consider this information as well when calculating the respective accuracy scores.

In a further embodiment of the invention, eye tracking is performed, wherein a present point of regard is calculated in dependency on a signal, especially the signal indicating the dominant eye. So, if during eye tracking, i.e. after the calibration; and/or validation procedures have been finished, the present point of regard of a user is repeatedly determined. This present point of regard can be advantageously determined in dependency on the information about the dominant eye. If, for example, the signal indicates that the left eye is the dominant eye, the present point of regard of the user can be calculated on the basis of only the data concerning the left eye to get better tracking results, or in other words the present point of regard can be calculated similar to the left point of regard described above, e.g. using only the determined left eye gaze vector. If the signal indicates that both eyes are equally dominant, then the present point of regard can be calculated as binocular present point of regard on the basis of the information concerning the left as well as the right eye. Therefore, eye tracking can be performed much more precisely and more robustly, which furthermore enhances also all the applications controlled by eye tracking, for example when the eye tracking system is used for controlling a mouse with a determined point of regard or for activating an element in a graphical user interface or also for selecting a focus point corresponding to the focus point of the user, and the like.

So preferably, the present point of regard is calculated with respect to the left eye if the left eye was determined as being dominant, the present point of regard is calculated with respect to the right eye if the right eye was determined as being dominant, and the present point of regard is calculated with respect to both eyes if none of the left and right eye was determined as being dominant.

In a further advantageous embodiment of the invention, the present point of regard is calculated as a weighted average between left eye data and right eye data, wherein weights of the weighted average are a function of the determined left accuracy score and right accuracy score, so that the right eye data is more heavily influencing the weighted average than the left eye data if the right accuracy score is higher than the left accuracy score, and the left eye data is more heavily influencing the weighted average than the right eye data if the left accuracy score is higher than the right accuracy score. The calculation of the present point of regard as a weighted average gives much more flexibility with regard to the optimization of the accuracy and even better results can be achieved. Especially because the binocular point of regard is much more robust than just calculating the point of regard only based on left eye data or only based on right eye data, this makes it possible that the data concerning both eyes can be used and still differences with regard to the accuracy of the respective eye can be taken into account.

The invention further relates to en eye tracking system for determining if one of a left and a right eye of a user is dominant, wherein the eye tracking system is configured to capture at least one image of the left and the right eye of the user, based on the at least one image and according to a predefined accuracy function to determine a left accuracy score for the left eye and a right accuracy score for the right eye and to determine if one of the left and the right eye of the user is dominant in dependency on at least the left and the right accuracy score.

The preferred embodiments and advantages thereof described with regard to the method for operating an eye tracking system according to the invention correspondingly apply to the eye tracking system according to the invention. In particular, the described steps of the method for operating an eye tracking system and its embodiments according to the invention constitute further embodiments of the eye tracking system according to the invention. For example the eye tracking system can comprise a capturing unit, one or more cameras and/or image sensors, for capturing the at least one image and a processing unit for processing the captured images and determining the respective accuracy scores according to the predefined accuracy function and to determine if one of the left and the right eye of the user is dominant. Furthermore, the eye tracking system can comprise a display device for showing the set points of regard. Moreover, the eye tracking device can comprise one or more light sources for illuminating the eyes and to produce reflections on the eyes which are used to determine features of the eyes like gaze direction and/or point of regard and/or the position and/or orientation of the respective eye.

In the following, advantageous embodiments of the present invention are described in more detail with reference to the accompanying drawings.

Figure 2:
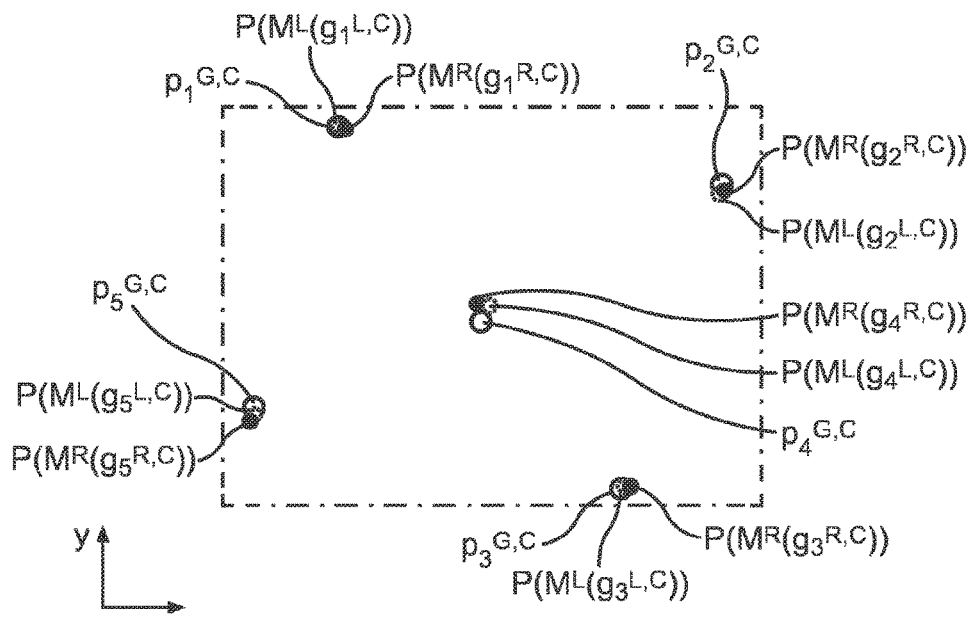
Figure 3A:
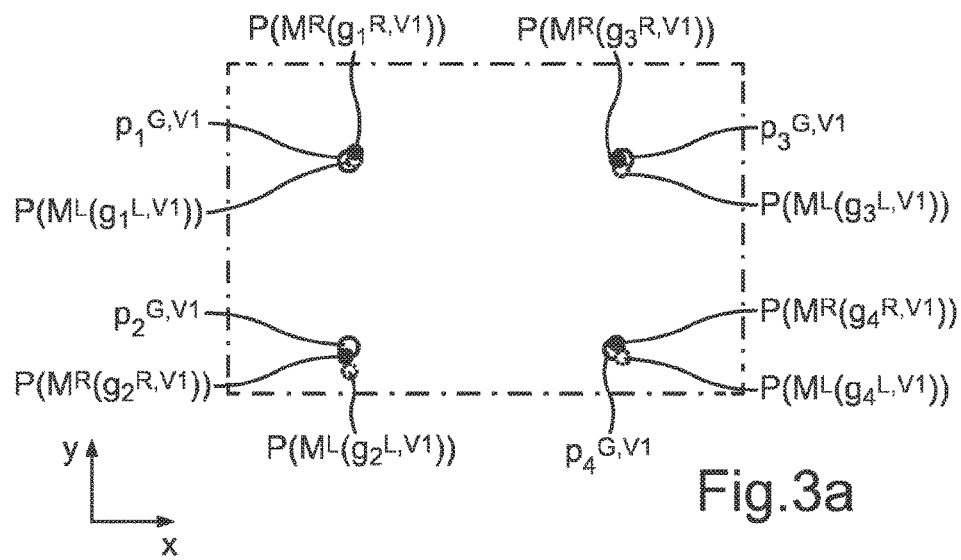
Figure 4:
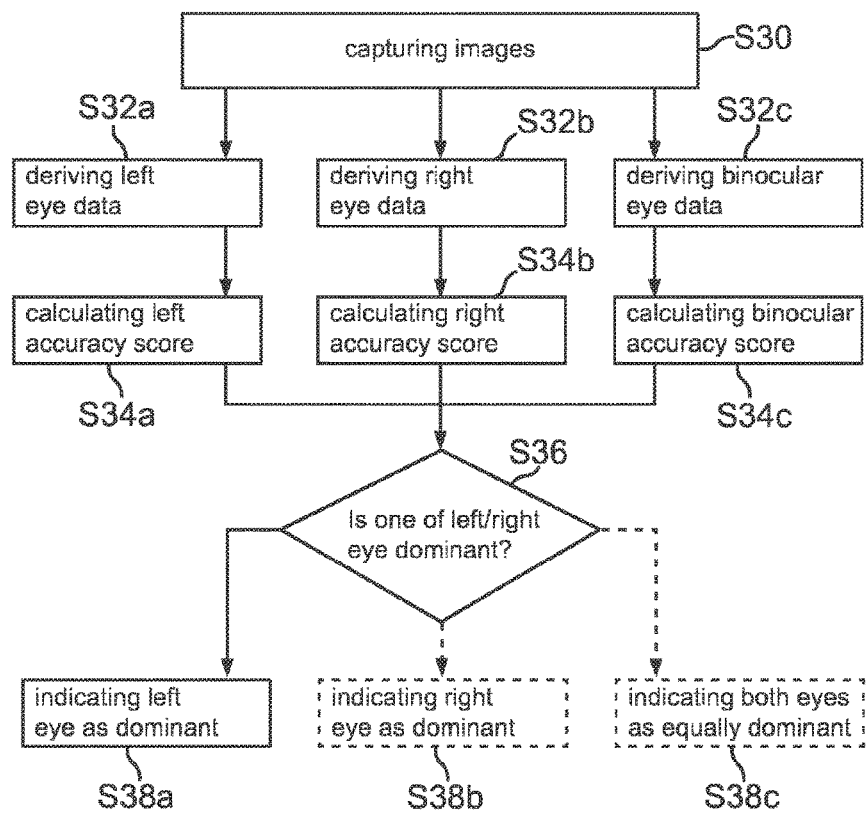
Figure 5:
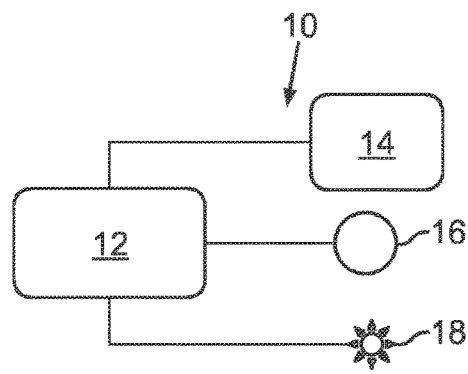

They show in:

FIG. 1 a schematic illustration of a method for operating an eye tracking system according to an embodiment of the invention;

FIG. 2 a schematic view of five calibration points shown on a display of an eye tracking system together with a determined point of regard for the left and the right eye each;

FIG. 3a a schematic view of four validation points shown on a display of an eye tracking system during a validation procedure together with a determined point of regard of the left and the right eye each according to an embodiment of the invention;

FIG. 3b a schematic view of four validation points shown on a display of the eye tracking system during a validation procedure together with a determined point of regard of the left and the right eye each according to an embodiment of the invention;

FIG. 4 a schematic illustration of the method for operating an eye tracking system, wherein a channel of the eye tracking system is chosen in dependency on the accuracy score of each channel according to an embodiment of the invention; and FIG. 5 a schematic view of an eye tracking system for determining the dominant eye of a user according to an embodiment of the invention.

In the following description of preferred embodiments for the previously used terms left set point of regard, right set point of regard and binocular set point of regard the term stimulus point is used as a synonym and furthermore, depending on whether these stimulus points are shown during a calibration procedure or validation procedure, these stimulus point are also called calibration points or validation points, respectively.

FIG. 1 shows a schematic view of a method for operating an eye tracking system 10 (compare FIG. 5) to determine the dominant eye of a user according to an embodiment of the invention. The method starts in step S10, where an input is received for starting a calibration procedure of the eye tracking system 10. This input can be a user input but also something different like a general starting signal. When this input is received, the eye tracking system 10 starts the calibration procedure. This calibration procedure can be performed as a standard calibration in step S12a or also optionally as a smart calibration in step S12b. Whether the standard calibration in step S12a or the smart calibration in step S12b is performed can also be indicated by the input signal in step S10.

If the user starts the standard calibration process, in step S12a stimulus points are shown at n predefined static positions on the stimulus plane and the user is supposed to look at these points. The stimulus plane can be a screen or an image plane of a display device of the eye tracking system, wherein the eye tracking system can be implemented as a remote eye tracker or also as a head mounted eye tracking device comprising head mounted displays. Thereby, the eye tracking system can also be configured to provide three dimensional images so that the stimulus plane not necessarily has to coincide with the physical screen plane of a display but can also be a virtual image plane produced by a 3D display or by stereoscopic displays. The position and orientation of this stimulus plane is known to the eye tracking system 10.

When the user looks at these stimulus points, the eye tracking system captures images of both eyes of the user and thereby, for example, can calculate the 3D position and/or orientation of each of the eyes and the gaze vectors of each of the eyes, wherein the point of regard of the left eye then is defined as the intersection of the gaze vector of the left eye with the stimulus plane, the right point of regard is defined as the intersection of the right eye gaze vector with the stimulus plane and the binocular point of regard can be defined as the intersection of a binocular gaze vector with the stimulus plane or also can be simply defined as the positional average of the left point of regard and the right point of regard on the stimulus plane. The stimulus points further are shown each at a time. The ground truth point of regards for these n stimulus points, which can also be denoted as set points of regard, are priorly known as $p^G_{i=1\sim n}$, which are normally represented by 2D vectors. From the eye tracking software accordingly n gaze samples $g^L_{i=1\sim n}$ from the left gaze channel, and n gaze samples $g^R_{i=1\sim n}$ from the right gaze channel are obtained. Each gaze sample $g_i$ includes all the eye and/or gaze information relevant to the $i^{th}$ calibration point.

The calibration has to produce a gaze correction model M: $g \rightarrow M(g)$ which maps the raw gaze samples to the calibrated ones. Especially there is produced a gaze correction model for the left eye $M^L$ and for the right eye $M^R$ each. The gaze correction model will ideally be able to correct all gaze samples from this user and the following gaze tracking.

Let the (priorly known) function that computes or extracts the point of regard from the gaze sample g be P: $g \rightarrow p = P(g)$. The gaze correction for the left eye $M^L$ is then optimized to minimize the difference between the calibrated point of regard $p^L = P(M^L(g^L))$ and the ground truth $p^G$, as $$\underset{M^L}{\operatorname{argmin}} \sum_{i=1}^{n} \|p_i^L - p_i^G\|^2 = \underset{M^L}{\operatorname{argmin}} \sum_{i=1}^{n} \|P(M(g^L)) - p_i^G\|^2 \quad (1)$$

The residual error of the left channel on the $i^{th}$ calibration point is computed as $$r_i^L = \|P(M^L(g_i^L)) - p_i^G\|. \quad (2)$$

The calibration is always done for the two monocular channels separately. Especially the same applies for the right channel in the same way and equations (1) and (2) also apply for the right channel if the index "L" is substituted by "R". Normally, the point of regard of the binocular gaze channel is created by averaging the left and right channels, as $$p^P = \frac{p^L + p^R}{2} = \frac{P(M^L(g^L)) + P(M^R(g^L))}{2}. \quad (3)$$

Therefore, the residual error for the binocular channel can be computed as $$r_i^B = \|p_i^B - p_i^G\|. \quad (4)$$

Instead of static stimulus points, the calibration can also be done by showing a continuously moving stimulus point. The path of the moving point is fully specified by a path model $p^G$, and this is the ground truth point of regard in the calibration. The gaze correction for the left eye $M^L$ is optimized to minimize the difference between the path of the calibrated point of regard and the ground truth path by doing a dynamic time warping:

$$\underset{M^L}{\operatorname{argmin}} \int_t \left\| p^L(t) - \min_{\substack{\Delta t \\ -T < \Delta t < T}} p^G(t + \Delta t) \right\|^2 dt = \quad (5)$$

$$\underset{M^L}{\operatorname{argmin}} \int_t \left\| P(M(g^L(t))) - \min_{\substack{\Delta t \\ -T < \Delta t < T}} p^G(t + \Delta t) \right\|^2 dt,$$

where T controls the maximal time window for matching.

The overall residual error of the left channel is exactly what we tried to minimize above $$r^L = \int_t \left\| p^L(t) - \min_{\substack{\Delta t \\ -T < \Delta t < T}} p^G(t + \Delta t) \right\|^2 dt. \quad (6)$$

Again the same applies for the right channel. The residual error for the binocular channel can be computed in a similar way after $$r^B = \int_t \left\| p^B(t) - \min_{\substack{\Delta t \\ -T < \Delta t < T}} p^G(t + \Delta t) \right\|^2 dt, \text{ with} \quad (7)$$

$$p^B = \frac{p^L + p^R}{2}.$$

So during the calibration process in step S12a the correction models $M^L$ and $M^R$ for the left and the right eye are calculated as well as optionally the errors $r^L$, $r^R$ and $r^B$ for the left channel, the right channel and the binocular channel, respectively. These results of the calibration process can then be outputted or provided in step S14 for further use by the eye tracking system, for example for a subsequent eye tracking and/or for a subsequent validation procedure.

These results can also directly be used for determining the dominant eye in step S22 in form of a self validation, which is explained later.

After the calibration procedure in step S12a is finished, the user can make an input in step S16 for activating a validation procedure, which then is performed in step S18 using the results of the calibration provided in step S14. Instead of a user input in Step S16 any other activation signal can be provided for activating the validation procedure. The validation procedure can also be started automatically after the calibration procedure is finished and step S16 can be omitted.

During the validation procedure, again stimulus points are shown on the stimulus plane but preferably at positions that are different from the positions of the calibration points.

While these stimulus points are shown, images of the eyes of the user are captured by the eye tracking system and eye features of each eye, like gaze vectors, are determined. Thereby, one again gets raw gaze samples $g^L_{j=1\sim m}$ for the left eye and $g^R_{j=1\sim m}$ for the right eye for each of the ground truth points of regard $p^G_{j=1\sim m}$, which are the positions of the stimulus points. Then the validation error for each channel, namely the error $r^R$ for the right channel the error $r^L$ for the left channel and the error $r^B$ for the binocular channel, is computed by applying the calibrated gaze correction model M, especially $M^L$ and $M^R$:

$$r_i^L = \|P(M^L(g_j^L)) - p_j^G\|, \quad (9)$$

$$r_i^R = \|P(M^R(g_j^R)) - p_j^G\|, \quad (10)$$

$$r_i^B = \left\| \frac{P(M^L(g_j^L)) + P(M^R(g_j^L))}{2} - p_j^G \right\|. \quad (11)$$

Instead of showing single stimulus validation points, again a validation stimulus point can be shown in a continuously moving manner as described with regard to the calibration procedure.

Furthermore, instead of the standard calibration described in step S12a, a smart calibration can be performed in step S12b. The reason for this is that due the distraction of the user or other problems, not all detected fixations in the calibrations procedure are good for the calibration purpose. Therefore, in the smart calibration a screening procedure can be implemented to detect and remove the "bad" calibration points. This feature provides higher calibration robustness and is also relevant to the calibration quality.

The smart calibration is similar to the standard calibration in that first of all multiple calibration stimulus points are shown on a stimulus plane, one after the other, and for each stimulus point the gaze and/or point of regard of the left eye, the right eye and the binocular gaze and/or point of regard is determined. The difference to the standard calibration is that not necessarily all of the stimulus points and the corresponding eye properties, like gaze and determined points of regard, are used for providing the correction model M.

Considering a set of n calibration points, the smart calibration procedure could be as follows:

First of all, all possible and interested subsets are enumerated. For example, when we have five points, all three-point, four-point and five-point subsets will be listed and evaluated in the following steps.

In the next step, for each calibration set three measures are considered: The number of calibration points, the quality (residual) of the calibration, and the deviation of the gaze correction from translation and scaling. There is also a prior knowledge based preference towards the subset consisting of more points. For a subset under testing, the calibration is done only using the points in the set, and then the corresponding residual error on the calibration set is computed. Empirically, bad calibration points often require a large "gaze correction" to minimize the residual. Therefore, a large deviation from a model that applies only translation and scaling is a sign of bad calibration points. All theses three measures will be combined into a score by a weighted sum. In the next step, among all the subsets the best one is selected based on their score. If the subset that consists of all points wins over all the other subsets, the calibration continues with all the n points. If this is not the case, the gaze correction model from the best subset will be used. The calibration points that are not in the selected subset will be labelled as "not used for bad quality".

This proposed approach is a reliable approach even for a small set of calibration points, e.g. five points. For a calibration with a large set of calibration points, e.g. more than eight, a more general sample consensus approach, for example RANSAC (Random Sample Consensus), can be used to detect the best subset.

So if finally the best subset is determined, the correction model M and residual errors as described for the standard calibration procedure in step S12a can be calculated, especially with regard to the chosen subset, and provided in step S14. If then the standard validation procedure is performed afterwards in step S18, the results of the smart calibration procedure are used similarly to those described above with regard to the standard calibration.

After this validation procedure in step S18, the validation results are provided in step S20 for determining the dominant eye of the user in step S22. Especially these validation results are the residual errors provided by (9), (10) and (11) or the respective overall residual errors in case of a smooth pursuit. Moreover, also the number of validly tracked points regarding each of the eyes can be provided as validation result.

With regard to determining the dominant eye, the basic idea is to evaluate the quality of each gaze channel based on the calibration and/or validation quality, and the best channel (binocular, left, right) can be chosen for eye tracking. If a validation procedure had been performed in step S18, the monocular validation error is the most natural quality measure for each monocular channel. The validation quality can also include the information about the number of well tracked validation points. So, based on the computed validation errors for each channel according to equations (9), (10) and (11), and further taking into account the number of well tracked validation points for each channel, an accuracy score can be determined for each of the channels. This accuracy score is the higher, the smaller the respective validation error and the higher the number of well tracked validation points is. Optionally, a "bonus", e.g. in form of a predefined numerical value, can be added to the accuracy score of the binocular channel so that in doubt the binocular gaze is usually more robust than the monocular gazes. Additionally, it could also be considered whether the numbers of valid gaze samples in the validation procedure is very unbalanced between the left and right channels, so that also information about the number of well tracked validation points can be used for calculating the respective accuracy scores. For example, it may be checked whether one channel has more than two times the number of tracked points compared with the other channel. If the left channel only gets two points tracked in the validation and the right channel gets five points, the system will switch to using the right channel for its better robustness. So, to determine the dominant eye, the system will compare the quality of the three channels based on the corresponding accuracy scores and pick the best one. The general rule is to use the best channel, while the validation quality is the most natural and reliable quality measure.

So, if the left channel is determined as the best channel, the left eye is determined to be the dominant eye. If the left and the right channel have equal or similar accuracy scores or the accuracy score of the binocular channel is the best one, then it is determined that both eyes are equally dominant or, in other words, that there is no dominant eye. Based on these results in step S22 an output signal in step S24 can be provided indicating the dominant eye. The signal then can be used for outputting the results of this determination on a screen or it can be used for a subsequent eye tracking by using the best channel.

In another embodiment, the validation procedure does not have to be performed necessarily. Optionally, the calibration results in step S14 can be used directly for determining the dominant eye in step S22 as a kind of self validation. So, this self validation allows for a gaze channel selection without additional validation. Thereby, the left and/or right and/or binocular gaze channel quality is determined based on the calibration quality. Therefore, the calibration results, especially the residual errors according to (2), for the left channel, the corresponding one for the right channel and the binocular residual error according to (4) or the respective overall residual errors according to (6) and (7) can be used to calculate the corresponding accuracy scores, which define the calibration quality for each channel. Also, the number of usable calibration points can be considered when calculating the respective accuracy scores. So, additionally, when the two channels have a different number of usable calibration points, wherein the reason could be smart calibration, loss of eye tracking, and so on, the channel with the fewer calibration points will be given a very low quality or accuracy score, for its calibration is much less reliable, even when its residual is smaller.

To sum up, the self validation is done on the calibration set, wherein the preferred solution is to use the calibration quality, i.e. the mean residual, as the validation quality. Another option would be the "leave-one-out cross-validation". Also, the calibration quality can include the information regarding the number of valid calibration points used in model fitting, since more calibration points generally result in a more accurate gaze correction. For providing the accuracy scores for each of the channels considering all or some of the above-mentioned quality influencing parameters, an accuracy function can be provided, wherein for example all these parameters can be summed up with corresponding weights. So, based on the so calculated accuracy scores for each channel, the dominant eye can be determined in the same way as described with regard to the results of the validation procedure and again a signal indicating the dominant eye can be outputted in step S24.

FIG. 2 shows a schematic view of five stimulus points shown in a stimulus plane during the calibration procedure together with the calibrated points of regard for the left and right eye each. The calibration points or stimulus points are denoted in FIG. 2 as $p_i^{G,C}$ for i=1, 2, 3, 4, 5. Furthermore, the determined and calibrated points of regard for the left eye are denoted by $P(M^L(g_i^{L,C}))$ for i=1, 2, 3, 4, 5 and the determined and calibrated points of regard for the right eye are denoted by $P(M^R(g_i^{R,C}))$. In FIG. 2 five stimulus points $p_i^{G,C}$ are shown for illustrative purposes all in one image, but during the calibration procedure these stimulus points $p_i^{G,C}$ are shown one at a time. Also, the shown calibrated points of regard $P(M^L(g_i^{L,C}))$, $P(M^R(g_i^{R,C}))$ are just for illustrative purposes and not shown during the calibration procedure. Actually, FIG. 2 can be seen as the result of the calibration procedure with the shown stimulus points $p_i^{G,C}$ and the corresponding determined and calibrated points of regard $P(M^L(g_i^{L,C}))$, $P(M^R(g_i^{R,C}))$.

As can be seen, for each stimulus point $p_i^{G,C}$ the point of regard $P(M^L(g_i^{L,C}))$, $P(M^R(g_i^{L,C}))$ of the left and the right eye can be determined. In this case, the number of validly tracked points of regard $P(M^L(g_i^{L,C}))$, $p(M^R(g_i^{R,C}))$ for the left and the right eye is five each. The residual error $r^L$ for the left channel can be determined as 0.5° in x-direction and 0.7° in y-direction, wherein the residual error $r^R$ for the right eye or right channel can be determined as 0.1° in x-direction and 0.5° in y-direction. These results could directly be used as self validation for determining the dominant eye, wherein in this example no dominant eye would be detected as the accuracies for the left and the right channel are quite similar.

Optionally, after this calibration procedure, a validation procedure can be performed using the calibration model M determined on the basis of the calibration procedure. Two examples of a validation procedure, especially their results, are shown in FIG. 3a and FIG. 3b.

In FIG. 3a four validation points are shown, which are denoted by $p_i^{G,V1}$ with i=1, 2, 3, 4, and which are different in their positions from the calibration points $p_i^{G,C}$. Furthermore, the points of regard relating to each of the validation points with respect to the right and the left eye each, which are determined during the validation procedure, are shown, too. The points of regard for the left eye are denoted by $P(M^L(g_i^{L,V1}))$ with i=1, 2, 3, 4, and the points of regard for the right eye are denoted by $P(M^R(g_i^{R,V1}))$. In this case, the average residual error $r^L$ for the left channel is 0.3° in the x-direction and 0.6° in the y-direction and the average residual $r^R$ error for the right channel is 0.2° in the x-direction and 0.3° in the y-direction. As these points of regard $P(M^L(g_i^{R,V1}))$ of the left and the right eye have comparable validation qualities in this example, the binocular channel is chosen for eye tracking or other purposes. Based on these validation results, it can be determined that none of the left and the right eye is a dominant eye.

In contrast thereto, FIG. 3b shows another example with different results of the validation procedure. Again, four validation points denoted by $p_i^{G,V2}$ with i=1, 2, 3, 4, are shown, which are again different in their positions from the calibration points $p_i^{G,C}$. Also, the points of regard with respect to the right and the left eye are shown, which are denoted by $P(M^L(g_i^{L,V2}))$ for the left eye and $P(M^R(g_i^{R,V2}))$ for the right eye, with i=1, 2, 3, 4. The average residual error $r^R$ for the right channel in this case is 0.7° for the x-direction and 0.6° for the y-direction, whereas for the left eye no useful points could be determined. In this case, as can be seen, the validation quality for the right eye is much better than for the left eye and tracking can be switched to monocular tracking with the better eye, in this case the right eye, using the right channel.

So, in general, if the difference between the validation qualities, which can be provided by calculating the corresponding accuracy scores, especially based on the respective errors, is above a predefined threshold, the better channel can be chosen for better robustness.

FIG. 4 shows a schematic illustration of a method for operating an eye tracking system according to another embodiment of the invention. In step S30 the eye tracking system captures images of both eyes of a user. This can be done by using one or more cameras. On the basis of the captured images, data relating to the left eye are derived in step S32a, with regard to the right eye in step S32c, and with regard to both eyes in step S32b. These data can, for example, be eye properties such as the position of the eyeball, the position of the pupil, the positions of eventually detected glints, the gaze direction and/or points of regard. Based on these data in each channel, namely for the left eye, the right eye and both eyes, a respective accuracy score is calculated for the left eye in step S34a, for the right eye in step S34c and for both eyes in step S34b. This accuracy score is a measure for the tracking quality in each channel. Based on these accuracy scores, in step S36 it is determined whether one of the left or the right eye is dominant. For example, if the left accuracy score and the right accuracy score are equal or their difference is below a predefined threshold, it is determined that none of the left and the right eye is dominant. If the left accuracy score is higher than the right accuracy score and optionally additionally the difference between the left and right accuracy score exceeds a predefined threshold, the left eye is determined as being dominant, especially except the binocular accuracy score is still higher than the left and the right one. The same applies for the right eye, namely if the right accuracy score is higher than the left accuracy score and optionally additionally the difference between the left and right accuracy score exceeds a predefined threshold, the right eye is determined as being dominant, especially except the binocular accuracy score is still higher than the left and the right one. In all other cases it would be determined that there is no dominant eye.

So, if for example it is determined in step S36 that the left eye is the dominant eye, a signal is provided in step S38a indicating the left eye as the dominant eye and eye tracking is performed using the left channel. If otherwise it would have been determined that the right eye is the dominant eye, a signal is outputted in step S38c indicating the right eye as the dominant eye and eye tracking is performed using the right channel. If in step S36 it would have been determined that no eye is dominant, a signal is outputted in step S38b indicating that no eye is dominant and both eyes or rather the binocular channel is used for eye tracking.

Alternatively, if one of the eyes is determined as dominant eye by the signal, it also would be possible to use the binocular gaze for eye tracking but wherein the binocular gaze is calculated on the basis of the left and right eye data, wherein the eye data of the dominant eye are weighted more heavily, e.g. the ratio of the weights could be or correspond to the ratio of the accuracy scores.

FIG. 5 shows a schematic view of an eye tracking system 10 according to an embodiment of the invention. The eye tracking system 10 comprises a processing or control unit 12, a display unit 14 and a capturing unit 16. Optionally, the eye tracking system 10 can comprise an illumination unit 18. The display unit 14 can be a monitor with a display, e.g. a computer monitor, or the eye tracking system 10 can be implemented as a head mounted display with an eye tracker. The capturing unit 16 can comprise one or more cameras capturing the eyes of a user. During a calibration and/or validation procedure of the eye tracking system 10, calibration points and/or validation points can be shown by means of the display unit 14. During the calibration and/or validation and for example also during subsequent eye tracking, the capturing unit 16 captures images of the eyes of a user. These images are then processed by the processing unit 12, which determines according to a predefined accuracy function a left accuracy score for the left eye and a right accuracy score for the right eye and optionally a binocular accuracy score for both eyes. Based on these accuracy scores, the processing unit 12 determines if one of the left and the right eye of the user is dominant. This result can be outputted on the display unit 14 or to be used for subsequent eye tracking. The illumination unit 18 can comprise one or more light sources, for example infrared LEDs, for illuminating the eyes of the user for the purpose of producing glints or other Purkinje images, which facilitates determining eye properties like the positions and orientations of eye features, the gazes, and so on.

To sum up, a method operating an eye tracking system and an eye tracking system is provided, by means of which advantageously the dominant eye of a user can be easily determined and which can be used for diagnostic purposes and especially for achieving much higher accuracy in eye tracking.

The invention claimed is:

1. A method comprising:
   capturing at least one image of a first eye of a user and a second eye of the user;
   determining, based on the at least one image, a first accuracy score for the first eye, a second accuracy score for the second eye, and a binocular accuracy score for both the first eye and the second eye; and
   determining, based on the first accuracy score, the second accuracy score, and the binocular accuracy score, an eye dominance characterization of the user, including:
      responsive to determining that the first accuracy score is greater than the second accuracy score and that the first accuracy score is greater than the binocular accuracy score, determining that the first eye of the user is dominant; or
      responsive to determining that the first accuracy score is within a predefined threshold amount of the second accuracy score or that the binocular accuracy score is greater than either of the first accuracy score or the second accuracy score, determining that no eye of the user is dominant.

2. The method of claim 1, wherein determining the first accuracy score for the first eye includes:
   determining a first set point of regard; and
   determining a deviation of a point of regard of the first eye based on the first set point of regard.

3. The method of claim 2, wherein determining the first set point of regard includes:
   displaying a plurality of eye tracking indicia at a respective plurality of locations on a display device at a respective plurality of times; and
   determining, for each of the respective plurality of times, a point of regard of the first eye as the user tracks the eye tracking indicia.

4. The method of claim 3, further comprising:
   determining a second set point of regard by determining, for each of the respective plurality of times, a point of regard of the second eye as the user tracks the eye tracking indicia; and
   determining a binocular set point of regard by determining, for each of the respective plurality of times, a point of regard of both the first eye and the second eye as the user tracks the eye tracking indicia.

5. The method of claim 1, further comprising:
   capturing at least one additional image of the first eye and the second eye; and
   determining, based on the at least one additional image and the eye dominance characterization of the user, a current point of regard of the user.

6. The method of claim 5, wherein determining the current point of regard is based on one or more of the first accuracy score, the second accuracy score, and the binocular accuracy score.

7. The method of claim 6, wherein determining the current point of regard includes:
   determining, based on the at least one additional image, a first eye data for the first eye,
   determining, based on the at least one additional image, a second eye data for the second eye;
   weighting the first eye data and the second eye data based on the first accuracy score and the second accuracy score; and
   determining the current point of regard based on the weighted first eye data and second eye data.

8. An apparatus comprising:
   at least one camera to capture at least one image of a first eye of a user and a second eye of user; and
   at least one processor to determine, based on the at least one image, a first accuracy score for the first eye, a second accuracy score for the second eye, and a binocular accuracy score for both the first eye and the second eye and to determine, based on the first accuracy score, the second accuracy score, and the binocular accuracy score, an eye dominance characterization of the user including:
      responsive to determining that the first accuracy score is greater than the second accuracy score and that the first accuracy score is greater than the binocular accuracy score, determining that the first eye of the user is dominant; or
      responsive to determining that the first accuracy score is within a predefined threshold amount of the second accuracy score or that the binocular accuracy score is greater than either of the first accuracy score or the second accuracy score, determining that no eye of the user is dominant.

9. The apparatus of claim 8, wherein the at least one processor is to determine the first accuracy score for the first eye by:
   determining a first set point of regard; and
   determining a deviation of a point of regard of the first eye based on the first set point of regard.

10. The apparatus of claim 9, wherein the at least one processor is to determine the first set point of regard by:
    displaying a plurality of eye tracking indicia at a respective plurality of locations on a display device of the apparatus at a respective plurality of times; and
    determining, for each of the respective plurality of times, a point of regard of the first eye as the user tracks the eye tracking indicia.

11. The apparatus of claim 8, wherein:
    the at least one camera is further to capture at least one additional image of the first eye and the second eye; and
    the at least one processor is further to determine, based on the at least one additional image and the eye dominance characterization of the user, a current point of regard of the user.

12. The apparatus of claim 11, wherein the at least one processor is to determine the current point of regard by:
    determining, based on the at least one additional image, a first eye data for the first eye,
    determining, based on the at least one additional image, a second eye data for the second eye;
    weighting the first eye data and the second eye data based on the first accuracy score and the second accuracy score; and
    determining the current point of regard based on the weighted first eye data and second eye data.

13. A non-transitory computer-readable medium having instructions encoded thereon which, when executed by a processing unit of an eye tracker, causes the eye tracker to:
    capture at least one image of a first eye of a user and a second eye of the user;
    determine, based on the at least one image, a first accuracy score for the first eye, a second accuracy score for the second eye, and a binocular accuracy score for both the first eye and the second eye; and
    determine, based on the first accuracy score, the second accuracy score, and the binocular accuracy score, an eye dominance characterization of the user, including:
        responsive to determining that the first accuracy score is greater than the second accuracy score and that the first accuracy score is greater than the binocular accuracy score, determining that the first eye of the user is dominant; or
        responsive to determining that the first accuracy score is within a predefined threshold amount of the second accuracy score or that the binocular accuracy score is greater than either of the first accuracy score or the second accuracy score, determining that no eye of the user is dominant.

14. The non-transitory computer-readable medium of claim 13, wherein the instructions, when executed by the processing unit of the eye tracker, cause the eye tracker to:
    display a plurality of eye tracking indicia at a respective plurality of locations on a display device at a respective plurality of times;
    determining, for each of the respective plurality of times, a point of regard of the first eye as the user tracks the eye tracking indicia; and
    determining a deviation of the point of regard of the first eye based on the point of regard of the first eye determined for each of the respective plurality of times.

15. The non-transitory computer-readable medium of claim 13, wherein the instructions, when executed by the processing unit of the eye tracker, cause the eye tracker to:
    capture at least one additional image of the first eye and the second eye; and
    determine, based on the at least one additional image and the eye dominance characterization of the user, a current point of regard of the user.

16. The non-transitory computer-readable medium of claim 15, wherein the instructions, when executed by the processing unit of the eye tracker, cause the eye tracker to:
    determine, based on the at least one additional image, a first eye data for the first eye,
    determine, based on the at least one additional image, a second eye data for the second eye;
    weight the first eye data and the second eye data based on the first accuracy score and the second accuracy score; and
    determine the current point of regard based on the weighted first eye data and second eye data.

* * * * *